United States Patent [19]

Lemere

[11] 4,207,882
[45] Jun. 17, 1980

[54] FILTER APPARATUS FOR WELDING MASK

[76] Inventor: Cordell T. Lemere, P.O. Box 7296, Olympia, Wash. 98507

[21] Appl. No.: 887,111

[22] Filed: Mar. 16, 1978

[51] Int. Cl.² ............................ A61F 9/06; A62B 7/10
[52] U.S. Cl. ....................................... 128/206.15; 2/9; 2/8
[58] Field of Search ......................... 2/8, 174, 206, 6, 5, 2/2.1 R, 2.1 A, 422, 424, 9; 128/142.7, 142.6, 146.6, 147, 141 R, 142 R, 142.5, 142.4

[56] References Cited

U.S. PATENT DOCUMENTS

| 652,080 | 6/1900 | Chappell | 128/142.7 |
|---|---|---|---|
| 1,975,797 | 10/1934 | Montuori | 128/142.6 |
| 1,978,994 | 10/1934 | Fortunato | 128/142.6 |
| 2,381,568 | 8/1945 | Booharin | 128/142.6 |
| 2,485,908 | 10/1949 | Morrow | 128/142.4 X |
| 3,118,445 | 1/1964 | Norman | 128/201.19 |
| 3,649,964 | 3/1972 | Schoelz et al. | 2/8 |
| 3,657,740 | 4/1972 | Cialone | 2/8 |

FOREIGN PATENT DOCUMENTS 431671 7/1935 United Kingdom .

Primary Examiner—Werner H. Schroeder
Assistant Examiner—Andrew M. Falik
Attorney, Agent, or Firm—Clarence A. O'Brien; Harvey B. Jacobson

[57] ABSTRACT

A filter apparatus for a welding mask having airways passage forming structure including a pair of filtered remote inlets and including an intermediate mouthpiece whereby filtered ambient air may be supplied to the mouthpiece. An exhaust structure is communicated at one adjacent point with the mouthpiece and includes a remote outlet. The outlet is provided with a one-way check valve as are each of the inlets and the airways passage forming structure from which the inlets and outlets are supported each comprise U-shaped clips for clampingly engaging an adjacent marginal portion of a welding mask.

11 Claims, 6 Drawing Figures

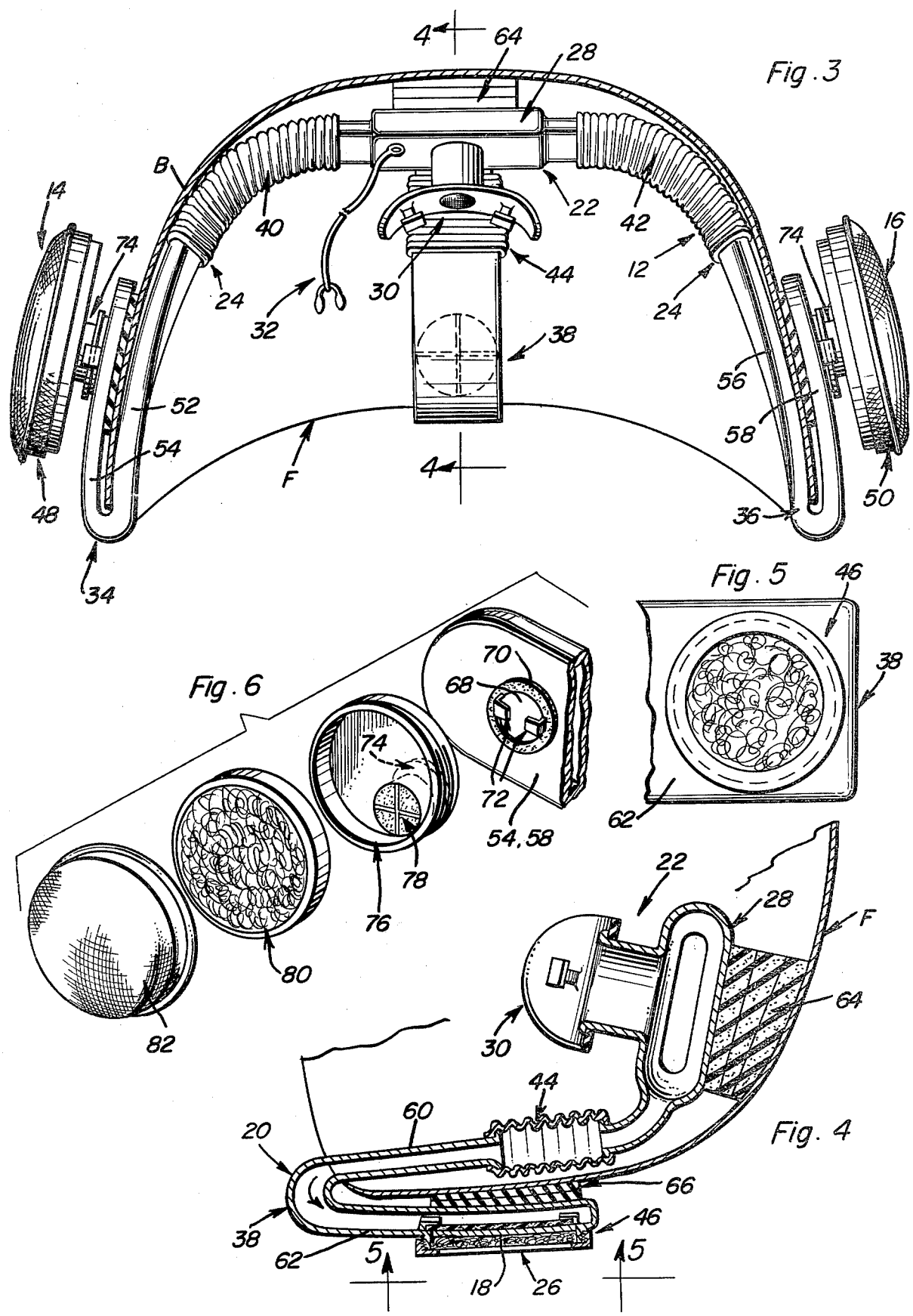

FILTER APPARATUS FOR WELDING MASK

BACKGROUND OF THE INVENTION

1. Field of the Invention

This invention relates generally to filter apparatus, and particularly to a filter attachment for use with welding and similar face masks.

2. Description of the Prior Art

A serious problem associated with welding operations is the protection of the welder from noxious fumes generated during the welding process. While masks are available on the market to protect the welder from such noxious fumes, these masks generally are quite heavy and very expensive, and accordingly there has been great resistance to their widespread use.

U.S. Pat. No. 3,535,703, issued Oct. 27, 1970, to H. R. Greenlee, discloses a welding helmet in which a fan assembly is disposed adjacent the mouth of a wearer of the helmet for drawing fresh air into the mask from a point generally behind the wear's head, and expelling the air through a forwardly directed opening adjacent the fan assembly.

U.S. Pat. Nos. 3,238,535, issued Mar. 8, 1966, 3,467,965, issued Sept. 23, 1969, 3,584,314, issued June 15, 1971, 3,649,964, issued Mar. 21, 1972, and 3,657,740, issued Apr. 25, 1972, disclose additional examples of face masks and helmets provided with air filtering devices.

SUMMARY OF THE INVENTION

It is an object of the present invention to provide a filter apparatus for a welding mask, and the like, which is simple and inexpensive of construction, yet reliable in operation.

It is another object of the present invention to provide a filter apparatus for a welding mask, and the like which is in the form of an attachment that can be removably mounted on a conventional mask, helmet and the like.

Yet another object of the invention is to provide a filter apparatus for welding masks, and the like, which can effectively filter the various particulate and gaseous pollutants encountered by a welder, and the like.

These and other objects are achieved according to the present invention by providing a filter apparatus having: an airways passage forming assembly including an inlet and an outlet and a filter for filtering air transmitted from the inlet to the outlet of the assembly; and a connector arrangement attached to the, and partially forming, the airways passage forming assembly for removably mounting the airways passage forming assembly on a conventional face mask, such as a welding mask, helmet, or the like.

The airways passage forming means includes a mouthpiece subassembly arranged for engagement by the mouth of a user of the apparatus, with a filter subassembly of the airways passage forming assembly being connected to the mouthpiece subassembly for filtering gases, such as air, drawn into the mouthpiece subassembly. The filter subassembly is disposed between the mouthpiece subassembly and the inlet of the airways passage forming means. An exhaust arrangement is connected to the mouthpiece subassembly for expelling exhaled gases received from the mouthpiece subassembly, with the exhaust arrangement being disposed between the outlet of the airway passage forming means and the mouthpiece subassembly.

The mouthpiece subassembly advantageously includes a manifold connected to the filter subassembly and the exhaust arrangement with a conventional mouthpiece being attached to the manifold for engagement by the mouth of the user of the apparatus.

The exhaust arrangement preferably includes a check valve disposed between the manifold of the mouthpiece subassembly and the outlet of the air-ways passage forming assembly for blocking gas flow from the outlet to the mouthpiece subassembly.

The connector arrangement is attached to the filter subassembly and the exhaust arrangement, and includes a plurality of hollow U-shaped clips partially forming the air flow path through the apparatus, and arrangeable embracing an edge of a face covering mask or helmet for retaining the air passage forming assembly on the mask or helmet.

The filter subassembly includes a filter mounted on an associated one of the clips, the clips each having a pair of legs and the filter and the check valve of the exhaust arrangement being mounted on one of the legs of a respective clip, which leg is disposed to be outside of the associated face mask or helmet.

Preferably, the filter subassembly includes a further filter different in nature from the one filter, but mounted on a respective one of the clips different than the one of the clips the filter is mounted on. The filter and further filter are disposed in opposed relation so as to be on spaced sides of an associated face mask or helmet, with the check valve of the exhaust arrangement and the one of the clips associated therewith being disposed substantially midway between the filter and further filter to form a symmetrical arrangement of the elements.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 3 is an enlarged, sectional view taken generally along the line 3—3 of FIG. 2.

FIG. 4 is an enlarged fragmentary, sectional view taken generally along the line 4—4 of FIG. 3.

FIG. 5 is a fragmentary view looking in the direction of the arrows 5—5 of FIG. 4.

FIG. 6 is a fragmentary, exploded, perspective view showing a filter assembly used with filter apparatus according to the present invention.

DESCRIPTION OF THE PREFERRED EMBODIMENTS

Figure 1:
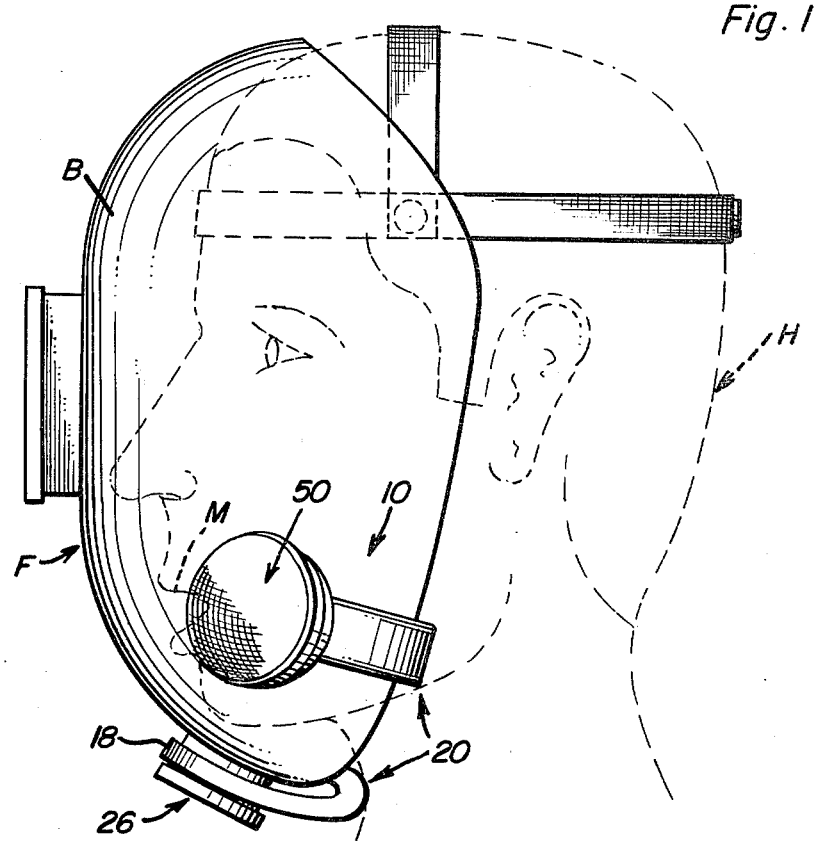
FIG. 1 is a schematic, side elevational view showing filter apparatus according to the present invention mounted on a face mask arranged on the head of a user.
Figure 2:
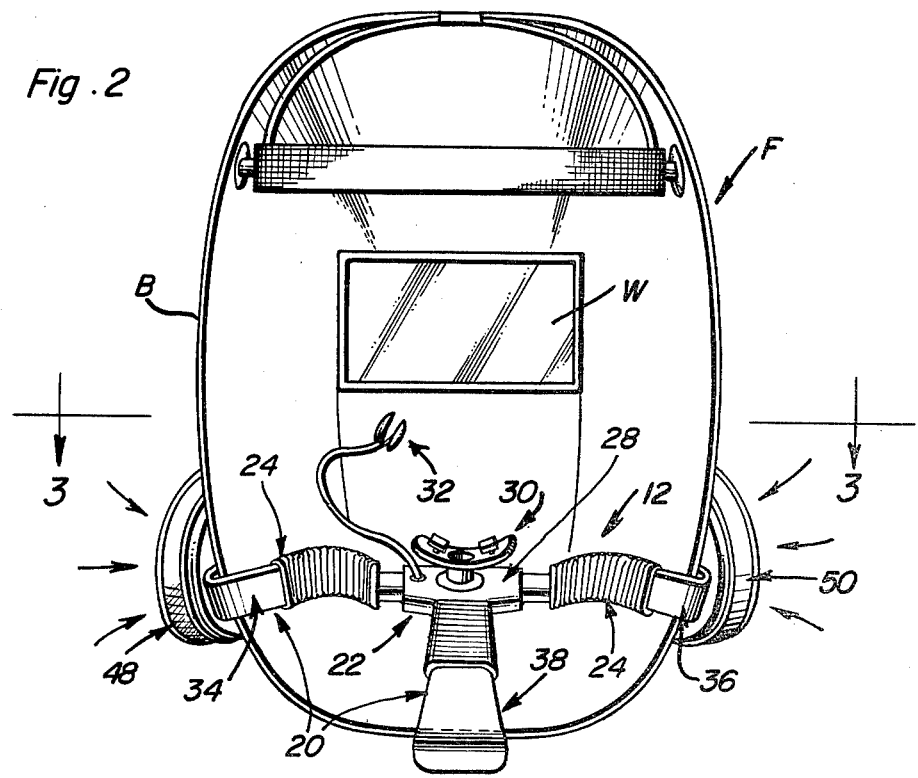
FIG. 2 is a rear elevational view showing the filter assembly and face mask seen in FIG. 1.

Referring now more specifically to FIGS. 1 through 5 of the drawings, a filter apparatus 10 according to the present invention includes an airways passage forming assembly 12 provided with inlets 14 and 16 and an outlet 18 for transmitting and filtering air. Attached to assembly 12 is a connector arrangement 20 for removably mounting assembly 12 on a face mask F illustrated as disposed in a conventional manner on the head H of a person using apparatus 10.

Assembly 12 includes a mouthpiece subassembly 22 arranged for engagement by the mouth M of a user of apparatus 10, and a filter subassembly 24 connected to mouthpiece subassembly 22 for filtering air drawn into mouthpiece subassembly 22 from the inlets 14 and 16 of assembly 12. Filter subassembly 24 is disposed between mouthpiece subassembly 22 and inlets 14 and 16, and in the illustrated embodiment the filter subassembly 24 actually partially forms the inlets 14 and 16. An exhaust arrangement 26 is connected to mouthpiece subassembly 22 for expelling air received therefrom, with exhaust arrangement 26 being disposed between, and actually forming, the outlet 18 of assembly 12.

Mouthpiece subassembly 22 includes a manifold 28 connected to filter subassembly 24 and to exhaust arrangement 26, with a conventional mouthpiece 30 being mounted on manifold 28. Mouthpiece 30 can be such as commonly employed with, for example, scubba diving equipment, and the like. In addition, a conventional nose plug 32 can be attached to manifold 28 for use by a user of apparatus 10, as desired.

Connector arrangement 20 includes a plurality of hollow U-shaped clips 34, 36, and 38 attached to the filter subassembly 24 and exhaust arrangement 26 by lengths of flexible tubing 40, 42, and 44, respectively.

These hollow clips 34, 36, and 38 partly from the air flow passage between the filter subassembly 24 and exhaust arrangement 26 and the manifold 28 of mouthpiece subassembly 22, and themselves are arrangeable embracing an edge of the shield or face plate portion B of a face mask F, and the like, for selectively retaining assembly 12 on the mask. Thus, it can be seen that apparatus 10 can be mounted on a conventional face mask or helmet in a simple manner.

Exhaust arrangement 26 includes a check valve 46 of conventional construction disposed between manifold 28 and outlet 18, which outlet 18 is formed by that portion of exhaust arrangement 26 providing an access opening to check valve 46, for blocking gas flow from outlet 18 to manifold 28 through the associated clip 38 and length of tubing 44. Further, filter subassembly 24 includes a pair of substantially identical filters 48 and 50, that differ only in the kinds of pollutants filtered out of an airways passing therethrough, mounted on an associated one of the clips 34 and 36. More specifically, the clips 34 and 36, as well as clip 38, each have a pair of legs, which legs are designated 52 and 54, 56 and 58, and 60 and 62. The filters 48 and 50 and check valve 46 are mounted on those legs 54, 58, and 62, respectively, which are disposed outside of the shield or face plate B of face mask F when apparatus 10 is clipped to the shield or face plate B. That is, the filters 48 and 50 as well as exhaust arrangement 26 are exposed externally of an associated face mask or helmet, while the mouthpiece subassembly 22 is disposed within the face mask or helmet.

In addition, the filters 48 and 50 are disposed in opposed relation to one another so as to be on spaced sides of an associated face mask or helmet, with exhaust arrangement 26 being disposed substantially midway between filters 48 and 50 so as to arrange the filter subassembly 24 and exhaust arrangement 26 in substantially symmetrical relation.

Resilient pad 64 and 66 are preferably provided on the outwardly, or frontly, facing surface of manifold 28 and on the inwardly facing surface of leg 62 of clip 38, respectively, for providing a cushion between apparatus 10 and the shield or face plate B of a face mask F.

Referring now more particularly to FIG. 6 of the drawings, each of the filters 48 and 50 is attached to an associated one of the legs 54, 58, which legs are in effect box manifolds each provided with a suitable opening 68 about which is disposed a sealing ring 70 provided with a conventional cam-lock 72 arranged for receiving a cam-lock neck 74 shown in full lines in FIG. 3, extending from a body 76 of the associated filter 48, 50. Arranged in the bottom surface of this body 76 is a conventional check valve 78 which permits gas flow only into the manifold formed by the associated leg 54, 58. The body 76 forms a receptacle for a filter cartridge 80, which is retained in the receptacle formed by the associated body 76 as by a conventional screen 82 formed in such a manner as to snap over or be threaded on the body 76. The filter cartridge 80 is of conventional construction to filter from the incoming gases such pollutants as poisonous gases and microparticles.

Check valve 46 can be constructed as a conventional resilient membrane which closes when a pressure differential is exerted across the membrane in one direction, but opens when a pressure differential is exerted across the membrane in the opposite direction.

As can be readily understood from the above description and from the drawings, a filter apparatus according to the present invention provides a simple inexpensive, yet reliable and lightweight device usable with conventional masks and helmets to protect a user from noxious gases and particulate matter in a polluted environment.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. An air filtering apparatus for a face mask including airway passage means for transmitting and passing filtered air, connector means attached to the airway passage means for removably mounting the airway passage means on a face mask, the connector means including a plurality of hollow U-shaped clips forming air flow paths therethrough and being part of the airway passage means, the clips each having a pair of legs arrangeably embracing an edge and on spaced sides of a face covering mask for retaining the air passage means on the mask.

2. Apparatus as defined in claim 1, wherein the air passage means includes exhaust means comprising a check valve arranged for blocking air flow into the airway passage means.

3. Apparatus as defined in claim 1, wherein the airway passage means includes filter means comprising a filter arranged for filtering air flow passing into the airway passage means.

4. Apparatus as defined in claim 3, wherein the filter means includes a further filter mounted in spaced relation with respect to the one filter.

5. Apparatus as defined in claim 1, wherein the airways passage means includes filter means and exhaust means placed in communication with one another, with the connector means being attached to the filter means and exhaust means.

6. Apparatus as defined in claim 1, wherein the airway passage means includes a mouthpiece means for engagement by the mouth of a user, and the airway passage means further includes a flexible tubing arranged connecting the clips to the mouthpiece means.

7. An air filtering apparatus for a face mask including airway passage means for transmitting and passing filtered air, connector means attached to the airway passage means for removably mounting the airway passage means on a face mask, said airway passage means including mouthpiece means for engagement by the mouth of a user of the apparatus and filter means connected to the mouthpiece means for filtering air drawn into the mouthpiece means, the airway passage means having an inlet, the airway passage means being disposed between the mouthpiece and the filter means, exhaust means connected to the mouthpiece means for expelling used air received from the mouthpiece means, the airway passage means having an outlet, the exhaust means being disposed between the outlet of the airway passage means and the mouthpiece means, the connector means being attached to the filter means and exhaust means, the connector means including a plurality of hollow U-shaped clips fastened to the filter means and exhaust means and forming air flow paths therethrough, the clips thus partially forming the airway passage means, and the clips arrangeably embracing an edge of a face covering mask for retaining the air filtering apparatus on the mask.

8. Apparatus as defined in claim 6, wherein the airway passage means further includes flexible tubing arranged connecting the clips to the mouthpiece means.

9. Apparatus as defined in claim 6, wherein the exhaust means includes a check valve disposed between the mouthpiece means and the outlet of the air passage means for blocking air flow from the outlet to the mouthpiece means.

10. Apparatus as defined in claim 4, wherein the filter means includes a filter body mounted on an associated one of the clips, the clips each having a pair of legs, and the check valve of the exhaust means being mounted on one of the legs of a respective clip, which one of the legs is arrangeable abutting the outside surface of an associated face mask.

11. Apparatus as defined in claim 7, wherein the filter means includes a further filter mounted on a respective one of the clips different from the one of the clips the first mentioned filter is mounted on, the filter and further filter being disposed in opposed relation so as to be on spaced sides of an associated face mask, with the exhaust means and the one of the clips associated therewith being disposed substantially midway between the filter and further filter.

* * * * *